US012566112B2

(12) United States Patent
Horn

(10) Patent No.: US 12,566,112 B2
(45) Date of Patent: Mar. 3, 2026

(54) DISCRETE SOIL SAMPLER

(71) Applicant: Jack Horn, Thornton, CO (US)

(72) Inventor: Jack Horn, Thornton, CO (US)

(73) Assignee: Jack W. Horn, Thornton, CO (US)

( * ) Notice: Subject to any disclaimer, the term of this patent is extended or adjusted under 35 U.S.C. 154(b) by 336 days.

(21) Appl. No.: 18/318,015

(22) Filed: May 16, 2023

(65) Prior Publication Data

US 2023/0375442 A1 Nov. 23, 2023

Related U.S. Application Data

(60) Provisional application No. 63/364,872, filed on May 17, 2022.

(51) Int. Cl.
G01N 1/08 (2006.01)
G01N 33/24 (2006.01)

(52) U.S. Cl.
CPC .............. G01N 1/08 (2013.01); *G01N 33/24* (2013.01)

(58) Field of Classification Search
CPC .................................. G01N 1/08; G01N 33/24
USPC ............ 73/864.44, 864.45; 175/20, 403, 405
See application file for complete search history.

(56) References Cited

U.S. PATENT DOCUMENTS 2,283,650 A * 5/1942 Sanborn ................... E21B 49/02
                                                          175/23
2,382,992 A * 8/1945 Harris ..................... E21B 49/02
                                                          175/21

3,042,124 A * 7/1962 Andersson ................ E21B 7/26
                                                          175/20
3,696,873 A    10/1972 Anderson
3,822,952 A * 7/1974 Johansson ........... E21B 17/0426
                                                          403/307
4,456,079 A * 6/1984 Rassieur ................. E21B 25/04
                                                          175/203
4,653,336 A    3/1987 Vollweiler
4,657,445 A    4/1987 Bossler
4,729,437 A    3/1988 Zapico
4,936,708 A * 6/1990 Perry ...................... E21B 47/13
                                                          405/184
4,946,000 A * 8/1990 Gibson ................... E21B 25/10
                                                          175/251
5,004,055 A    4/1991 Porritt et al.
(Continued)

FOREIGN PATENT DOCUMENTS

EP          0305178          3/1989

*Primary Examiner* — John Fitzgerald
(74) *Attorney, Agent, or Firm* — Jack W Horn; INVENTER

(57) ABSTRACT

An example discrete soil sampler includes a sample core barrel and a soil cutting shoe connected to the driving end of the sample core barrel. The example discrete soil sampler also includes a collection tube attached to the second end of the soil cutting shoe for inserting into the cylinder body of the sample core barrel when the soil cutting shoe is attached to the driving end of the sample core barrel. The example discrete soil sampler also includes a sample drive rod having a pointed end. The sample drive rod is movable through the cylinder body of the sample core barrel until the pointed end extends out through an opening formed through the cutting edge of the soil cutting shoe. The sample drive rod is retracted and the sample core barrel drilled down further to obtain the soil sample.

14 Claims, 17 Drawing Sheets

(56) References Cited

U.S. PATENT DOCUMENTS

| 5,186,263 A * | 2/1993 | Kejr | E21B 7/26 |
| | | | 175/58 |
| 5,419,211 A * | 5/1995 | Rodel | E21B 11/005 |
| | | | 73/864.45 |
| 5,488,876 A * | 2/1996 | Casey | E21B 33/127 |
| | | | 73/864.45 |
| 5,542,481 A * | 8/1996 | Scott | E21B 49/02 |
| | | | 175/23 |
| 5,854,432 A * | 12/1998 | Vollweiler | G01N 1/08 |
| | | | 73/864.44 |
| 6,357,535 B1 | 3/2002 | Lemon | |
| 6,393,926 B1 * | 5/2002 | Bowersox, Jr. | B01L 3/0217 |
| | | | 73/864.64 |
| 6,695,075 B2 * | 2/2004 | Beeker | E21B 25/06 |
| | | | 175/58 |
| 7,575,069 B2 * | 8/2009 | Pavlik | E21B 7/027 |
| | | | 175/323 |
| 9,068,409 B2 | 6/2015 | Mohamed | |
| 2003/0205408 A1 * | 11/2003 | Lee | G01N 1/08 |
| | | | 175/20 |

* cited by examiner

DISCRETE SOIL SAMPLER

PRIORITY CLAIM

This application claims the priority filing benefit of U.S. Provisional Patent Application No. 63/364,872 filed May 17, 2022 for "Discrete Soil Sampler" of Jack Horn, hereby incorporated by reference in its entirety as though fully set forth herein.

BACKGROUND

Proper soil sampling techniques are critical to determine the average nutrient status in a field, as well as the nutrient variability across a field. Fertilizer recommendations based on samples that are not representative of a field may result in over-application and/or under-application of nutrients. This can have a negative impact on both economics and the environment. There are other reasons for taking below-ground level samples of soil and/or components (e.g., locating a well, oil and gas drilling operations, etc.).

DETAILED DESCRIPTION

Figure 1:
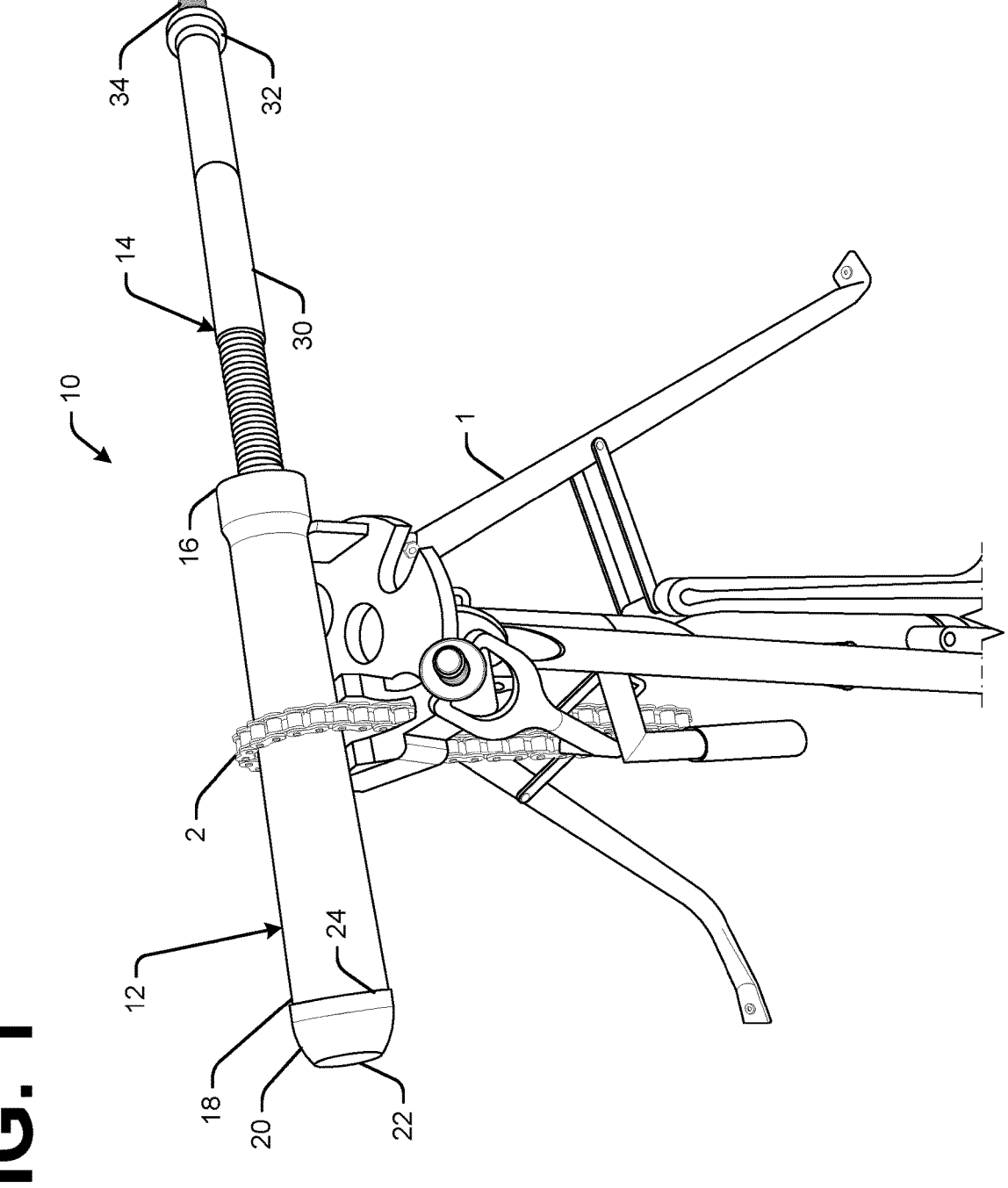
FIG. 1 shows an example discrete soil sampler as it is resting on a work stand.

A discrete soil sampler is disclosed. Although described herein with reference to sampling soil, it is understood that the term soil as used herein applies to what might traditionally be referred to as soil and/or other components of the ground. These samples are also referred to as cores, and include any sample taken below the surface level of the ground (e.g., by drilling into the earth). In addition, the discrete soil sampler may be implemented to take samples for any purpose (e.g., agriculture, oil/gas drilling, water table analysis, water wells, site cleanup, chemical or other toxic material spills, etc.).

An example discrete soil sampler includes a sample core barrel having a cylinder body with a threaded receiving end and a threaded driving end. The example discrete soil sampler also includes a soil cutting shoe having a cutting edge and removably attached to the sample core barrel. A collection tube is attached to the soil cutting shoe and inserted into the cylinder body of the sample core barrel when the soil cutting shoe is attached to the driving end of the sample core barrel.

The example discrete soil sampler also includes a threaded sample drive rod having a pointed end. The sample drive rod is threaded through the receiving end and through the cylinder body of the sample core barrel until the pointed end extends out through an opening formed through the cutting edge of the soil cutting shoe. The example discrete soil sampler also includes an attachment end of the sample drive rod to mate with a drill extension rod.

In an example, the discrete soil sampler may be operated with a drill rig. The threading may be a dual percussion drill rod thread.

During operation, the sample drive rod is drilled into a ground layer until the sample drive rod reaches a depth from which a soil sample is to be obtained. Upon reaching the depth from which the soil sample is to be obtained, the sample drive rod is retracted from the collection tube, and the sample core barrel is then drilled deeper into the ground layer to collect the soil sample in the collection tube. The sample core barrel is then removed from the ground layer, and once returned above ground, the soil sample can be removed from the collection tube.

The example discrete soil sampler can be opened and deployed, ready for soil sampling quickly upon arrival at its determined depth into the sub-surface being sampled. The example discrete soil sampler does not require any extruder rods for opening.

The example discrete soil sampler can be driven into the soil with several different types of machines. The example discrete soil sampler, when open, adds direct weight of the shank (or sampler drive rod) above the sample core barrel, for maximum core penetration.

In an example, the shank (or sampler drive rod) enables the example discrete soil sampler to obtain various core sample barrels (e.g., ranging from about 1 foot to about 2 feet in length). Different core sample lengths can also be provided. In an example, more than one core sample barrel may be implemented. Multiple core barrels can be mounted on the same sampler drive rod.

The example discrete soil sampler does not produce any extra soil cuttings, beyond the soil sample itself. It collects a determined amount of soil for the sample only. This reduces or altogether eliminates the need to dispose of contaminated soil, which can be very costly.

Before continuing, it is noted that as used herein, the terms "includes" and "including" mean, but is not limited to, "includes" or "including" and "includes at least" or "including at least." The term "based on" means "based on" and "based at least in part on."

Figure 2:
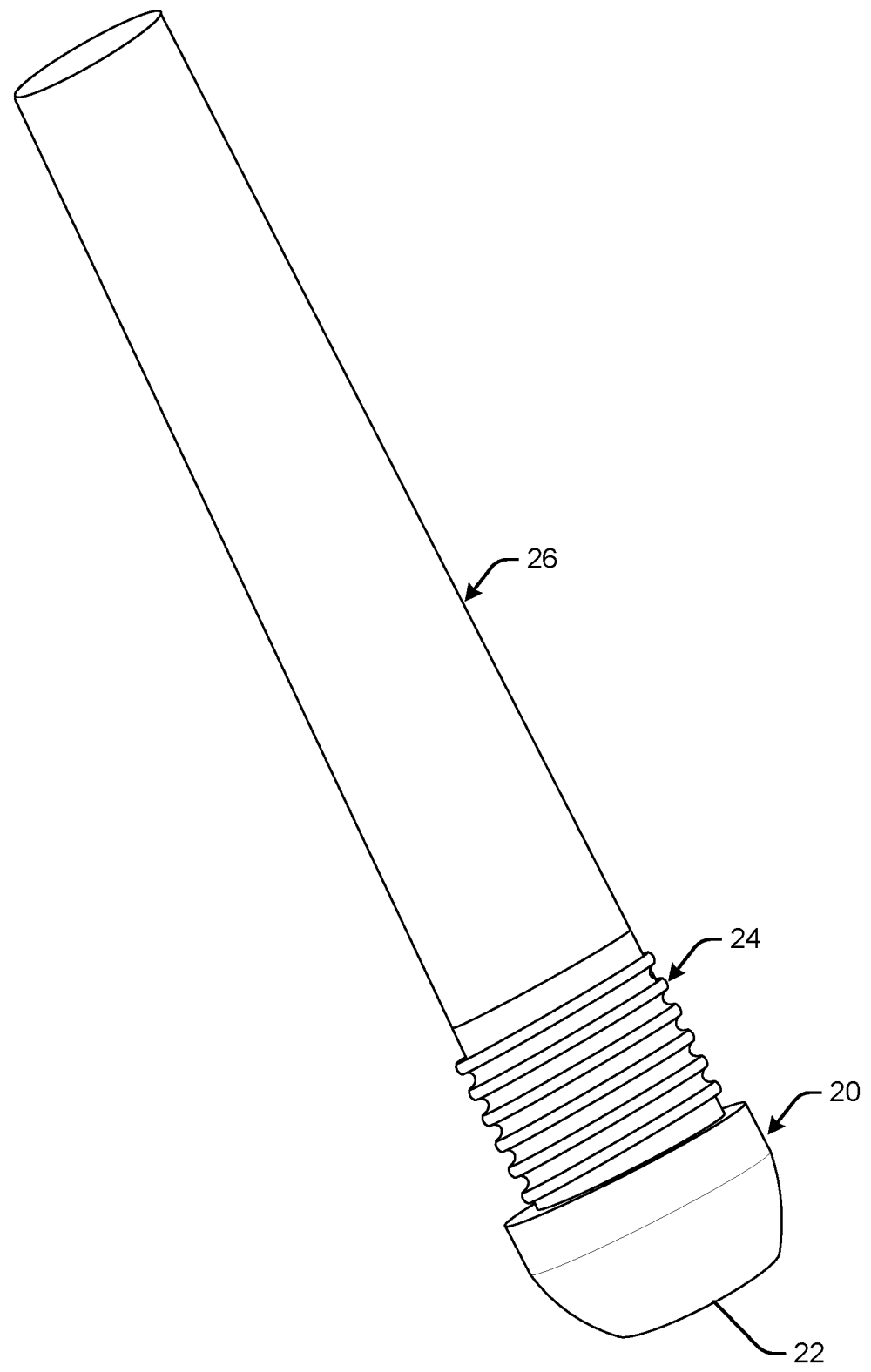
FIG. 2 shows an example collection tube of the example discrete soil sampler removed from the sample core barrel.
Figure 3:
FIG. 3 shows an example sample drive rod of the discrete soil sampler.
Figure 3:
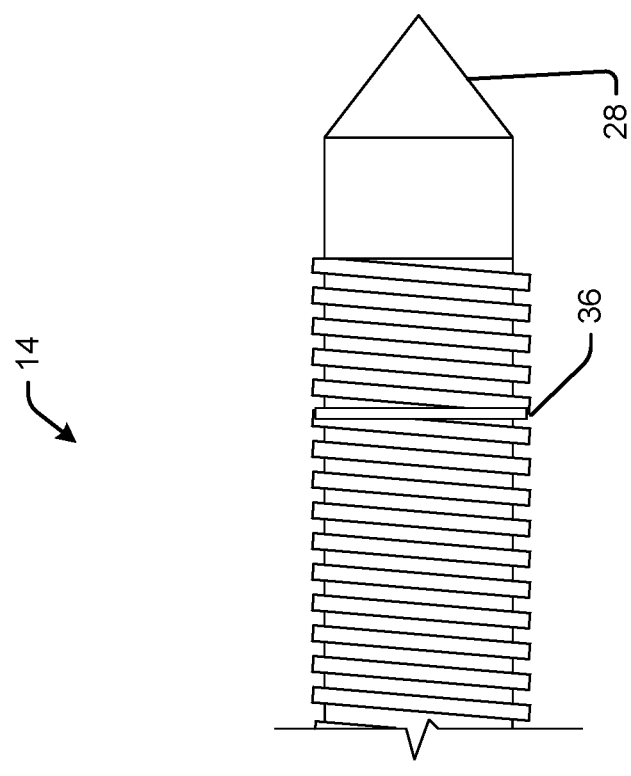
Figure 3:
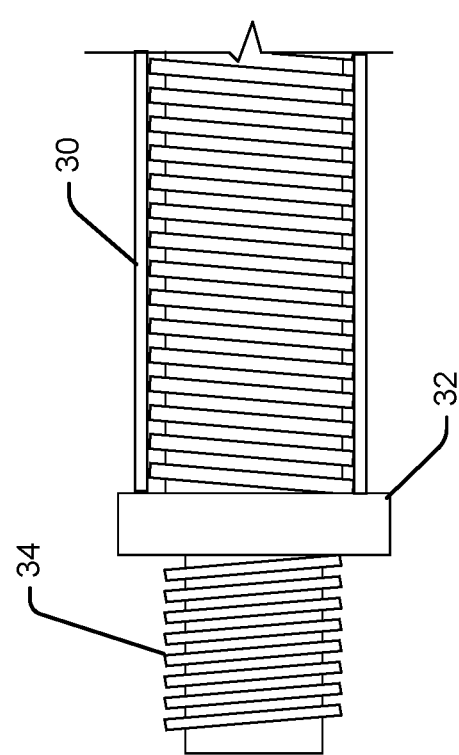
Figure 4:
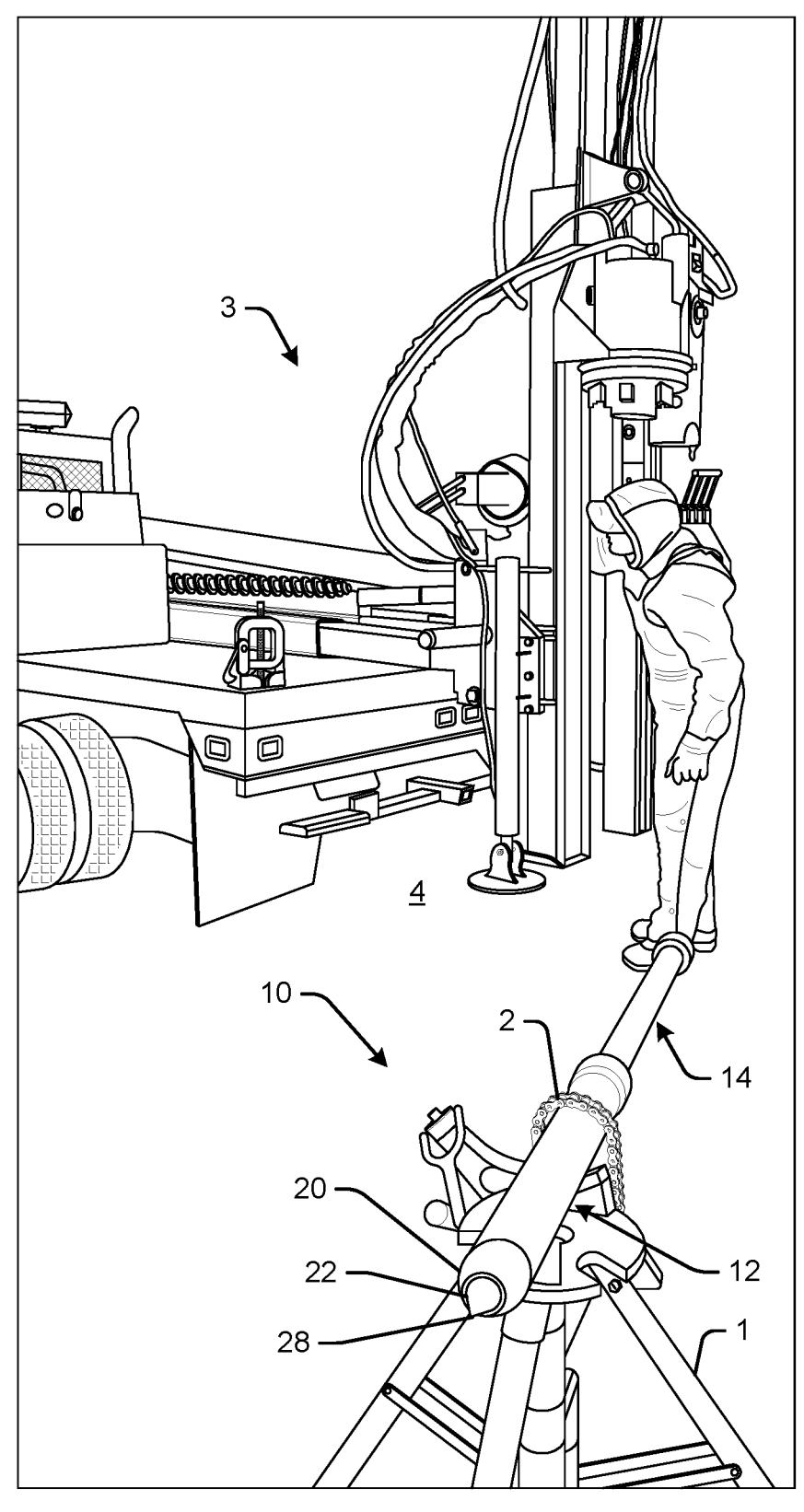
FIG. 4 shows the example discrete soil sampler and a rig on which it may be installed.
Figure 5:
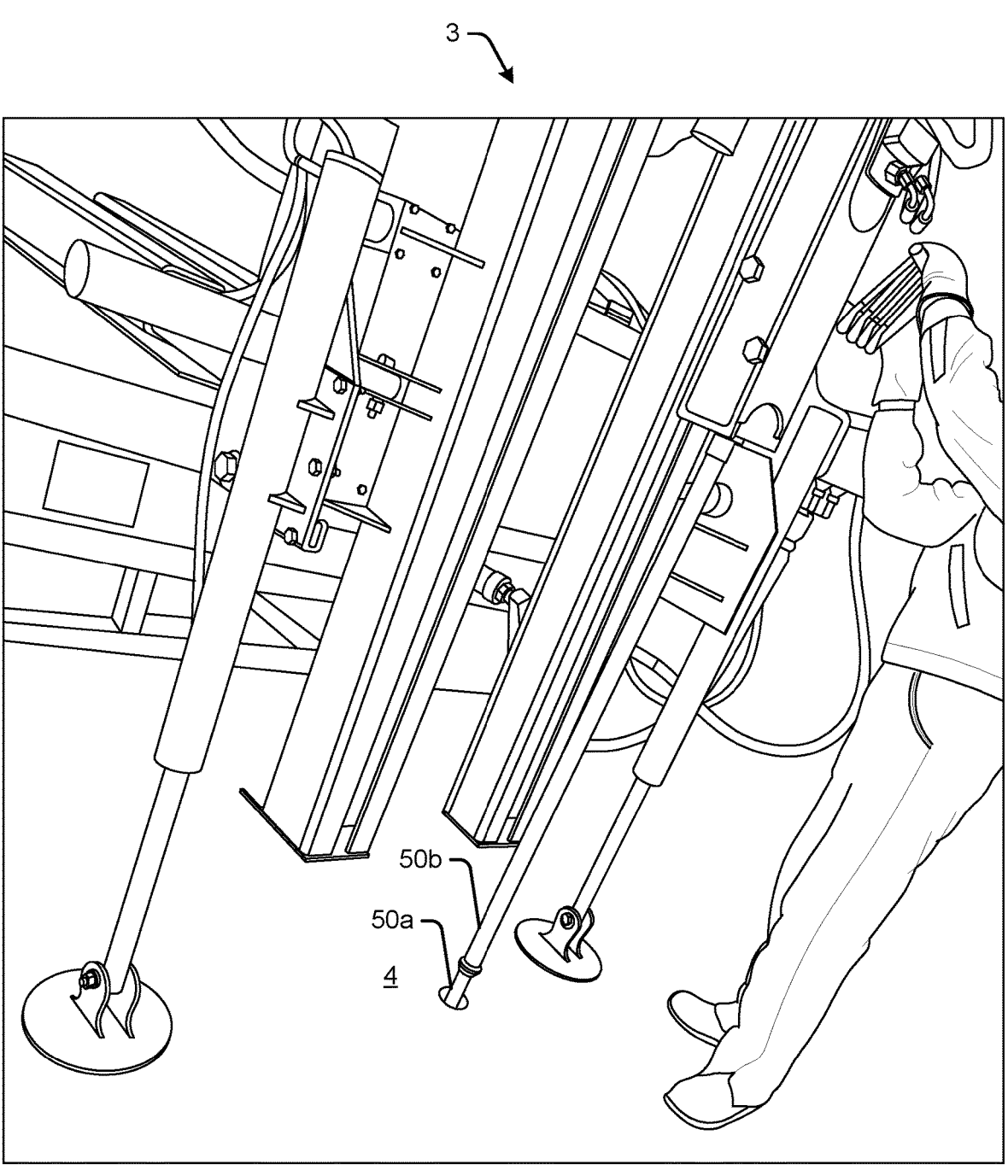
FIG. 5 shows the example discrete soil sampler installed on the rig for a drilling operation.

FIG. 1 shows an example discrete soil sampler 10 as it is resting on a work stand 1. The discrete soil sampler 10 is shown including a sample core barrel 12 and a sample drive rod 14. The chain 2 is shown simply as a means for retaining the discrete soil sampler 10 on the work stand 1, but does not form a part of the discrete soil sampler 10. Nor is the work stand 1 a part of the discrete soil sampler 10. FIG. 2 shows an example collection tube of the example discrete soil sampler removed from the sample core barrel. FIG. 3 shows an example sample drive rod 14 of the discrete soil sampler 10. FIG. 4 shows the example discrete soil sampler 10 and a rig 3 on which it may be installed. FIG. 5 shows the example discrete soil sampler 10 (below ground) as it may be installed on the rig 3 for a drilling operation. The example discrete soil sampler 10 may be implemented for collecting soil samples beneath the surface of the ground 4.

In an example, the discrete soil sampler 10 may be implemented with direct push or percussion drilling machines (e.g., rig 3). The discrete soil sampler 10 can be implemented with all hollow stem auger drilling machines. The discrete soil sampler 10 may be a blow count rated soil sampler (e.g., the number of blows required to drive an object into soil), the most functionable and rugged subsurface soil sampler currently available. However, the discrete soil sampler 10 described herein is not limited to use with any particular type of drilling machine, and can be readily configured for use with any of a variety of drilling machines, now known or later developed, as will be readily appreciated by those having ordinary skill in the art.

An example of the discrete soil sampler 10 includes a sample core barrel 12 having a cylinder body with a receiving end 16 and a driving end 18. The example discrete soil sampler 10 also includes a soil cutting shoe 20 on the driving end 18 of the sample core barrel 12. It is noted that the upper end of the sample core barrel 12 is where there are 1.5 inch left handed acme internal threads that allow locking the sampler drive rod 12 against the removable soil cutting shoe 20. The soil cutting shoe 20 is shown having a cutting edge 22 on a first end, and a second (e.g., threaded) end 24 for connecting to the driving end 18 of the sample core barrel 12.

The example discrete soil sampler 10 also includes a collection tube 26 (see FIG. 2) attached to the second end 24 of the soil cutting shoe 20 for inserting into the cylinder body of the sample core barrel 12 when the soil cutting shoe 20 is attached to the driving end 18 of the sample core barrel 12. The example sample core barrel 12 is 13 inches long. It is noted that sample core barrels may be various lengths. In an example, the upper end of the sample core barrel 12 has 1.5 inch left handed acme internal threads that enable locking the sampler drive rod against the removable soil cutting shoe 20. In an example, the removable soil cutting shoe 20 is manufactured with a conical shaped edge 22 on one end and a 1.875" O.D. dual percussion drill rod thread on the other. In an example, the sample core barrel 12, on the bottom end, is a 2.1875 O.D. hardened alloy steel tube with internal dual 1.875" I.D. dual percussion drill rod thread for threading in removable soil cutting shoe 20.

The example discrete soil sampler 10 also includes a sample drive rod 14 (see FIG. 3) having a pointed end 28. The sample drive rod 14 is inserted through the receiving end 16 of the sample core barrel 12, and is movable (e.g., threaded) at least part way through the cylinder body of the sample core barrel 12 until the pointed end 28 extends out through an opening formed through the cutting edge 22 of the soil cutting shoe 20.

The sampler drive rod (or shank) 14 enables the use of various core sample barrels (e.g., ranging from about 1 foot to about 2 foot). Any size core barrel 12 can be mounted on the same sampler drive rod to provide different core sample lengths.

In an example, the discrete soil sampler 10 includes a shank rod cover 30. The shank rod cover 30 may be a long, narrow part of a tool connecting the handle to the operational end. The shank rod cover 30 provides protection from soil and any other foreign contaminated substances that may be exposed to any part of the sampler drive rod 14. In an example, the shank rod cover 30 is a polycarbonate round tube that protects the exterior part of the sampler drive rod 14. In an example, the shank rod cover 30 has a 1.625 inch O.D.×1.50 inch I.D. The shank rod cover 30 may be provided in various lengths.

The sample drive rod 14 may be a precision acme threaded sample drive rod 14 manufactured with a conical shaped point 28 on a bottom end of the sample drive rod 14. These hardened alloy steel threads are broad, smooth, square and provide more strength when carrying heavier loads on the sample drive rod 14.

In an example, the sample drive rod 14 is configured to be drilled into one or more ground layer 4 until the sample drive rod reaches a depth from which a soil sample is to be obtained. On the top end of the sample drive rod 14 is a connection point or attachment 34 for drill rods. In an example, the sample drive rod 14 may be attached to an industry standard drill rod having a dual lead thread (1.5 inch O.D. thread) requiring 1 and ¾ turns to connect the drill rod to the sample drive rod 14.

The sample drive rod 14 requires no extruder rods for opening the sample containment area within the sample collection tube 26 shown in FIG. 2. In an example, the sample drive rod 14 is configured to be retracted from the collection tube 26 on reaching the depth from which the soil sample is to be obtained. In an example, the sample drive rod 14 includes an external retaining ring or collar 32 on the bottom end of the sample drive rod. The collar 32 provides a rotational stop to prevent the discrete soil sampler from being withdrawn too far from the sample area during operation.

The sample collection tube 26 may be a clear polycarbonate round tube for safe soil collection. The sample collection tube 26 keeps the soil samples safe during the collection and retrieval process of soil samples. The sample collection tube 26 can be attached to the dual percussion drill rod thread end of the soil cutting shoe 20 by an external flare cut on the end of the dual percussion drill rod thread.

After retracting the sample drive rod 14, the sample core barrel 12 is configured to be drilled deeper into the ground layer to collect the soil sample in the collection tube 26. In an example, the cutting edge 22 of the soil cutting shoe 20 is tapered to reduce moving soil down into a hole being drilled to preserve integrity of the soil sample.

Following sample collection, the sample core barrel 12 is configured to be removed from the ground layer(s) 4 so that the soil sample can be removed from the collection tube 26.

In an example, the sample core barrel 12 on the bottom end is a 2.1875 O.D. hardened alloy steel tube with internal dual 1.875" I.D. dual percussion drill rod thread for threading in removable soil cutting shoe 20.

In an example, the sample drive rod 14 includes an attachment end 34 configured to mate with a drill extension rod (e.g., 50a in FIGS. 7-10). The attachment end 34 may be configured as a connection point for all industry standard drill rods. For example, the attachment end 34 may include a dual lead thread 1.5 O.D. requiring 1 and ¾ turns to connect drill rods together.

In an example, the discrete soil sampler 10 includes a stop on the sample drive rod 14 to prevent the pointed end 28 from overextending out through the opening formed through the cutting edge 22 of the soil cutting shoe 20. For example, the stop on the sample drive rod may be a collar 32 (see, e.g., FIGS. 1 and 3).

Figure 12:
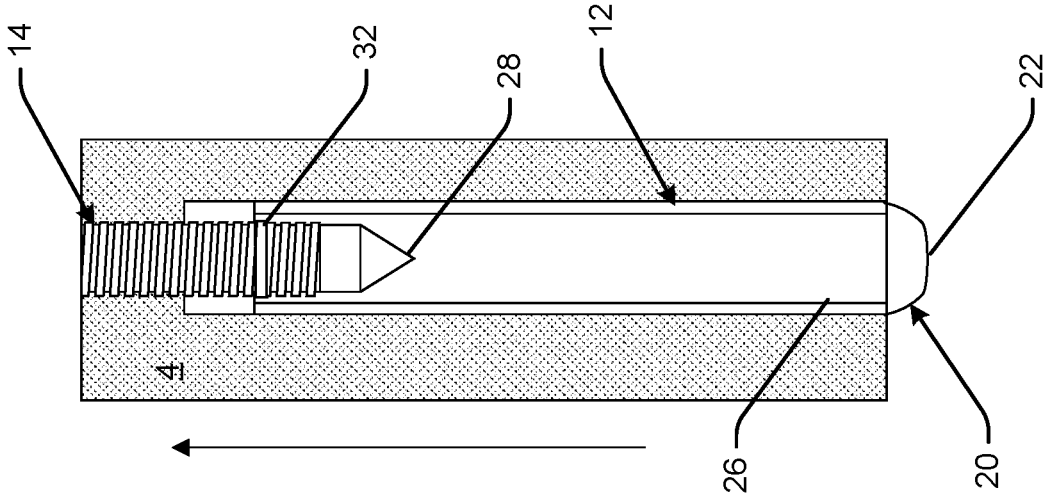
FIG. 12 is a close-up illustration showing the sample drive rod retracting in the sample core barrel during the example sampling operation.
Figure 12:
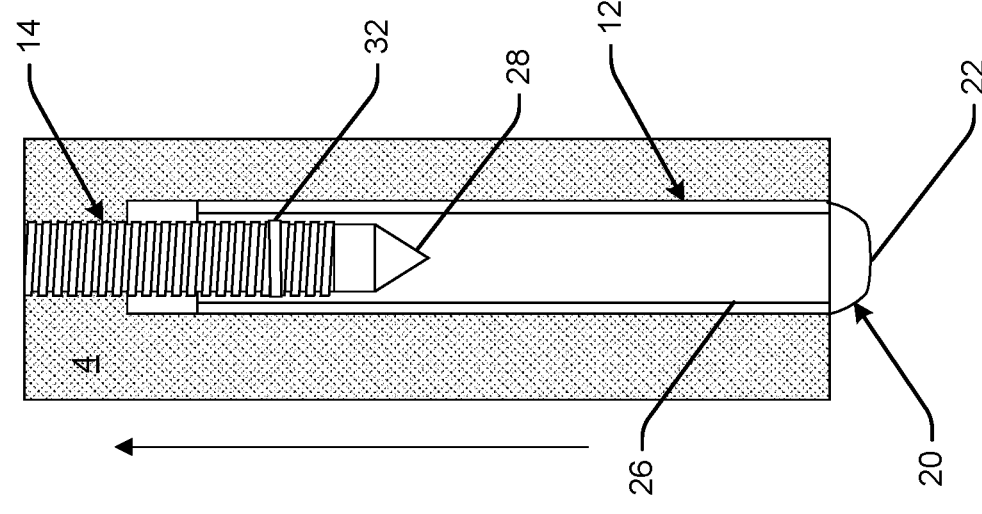

In an example, the discrete soil sampler also includes a stop on the sample drive rod 14 to prevent the drive rod 14 from being fully removed from the sample core barrel 12 (see e.g., FIG. 12). For example, the stop may be formed by a recessed internal cut 36 on a dual percussion drill rod thread of the sample drive rod 14 (see, e.g., FIG. 3).

It is noted that the examples described herein are provided for purposes of illustration, and are not intended to be limiting. Other devices and/or device configurations may be utilized to carry out the operations described herein.

An example sampling operation is described below with reference to FIGS. 6-17. The example discrete soil sampler 10 may be implemented with any drilling machines now known or later developed, such as but not limited to, direct push or percussion drilling machines. The following operations are described with reference to a hollow stem auger drilling machine 3 wherein the discrete soil sampler 10 is rated as a blow count rig (e.g., where blows are required to drive an object into soil).

The operations shown and described herein are provided to illustrate example implementations. It is noted that the operations are not limited to the ordering shown. Still other operations may also be implemented.

Figure 6:
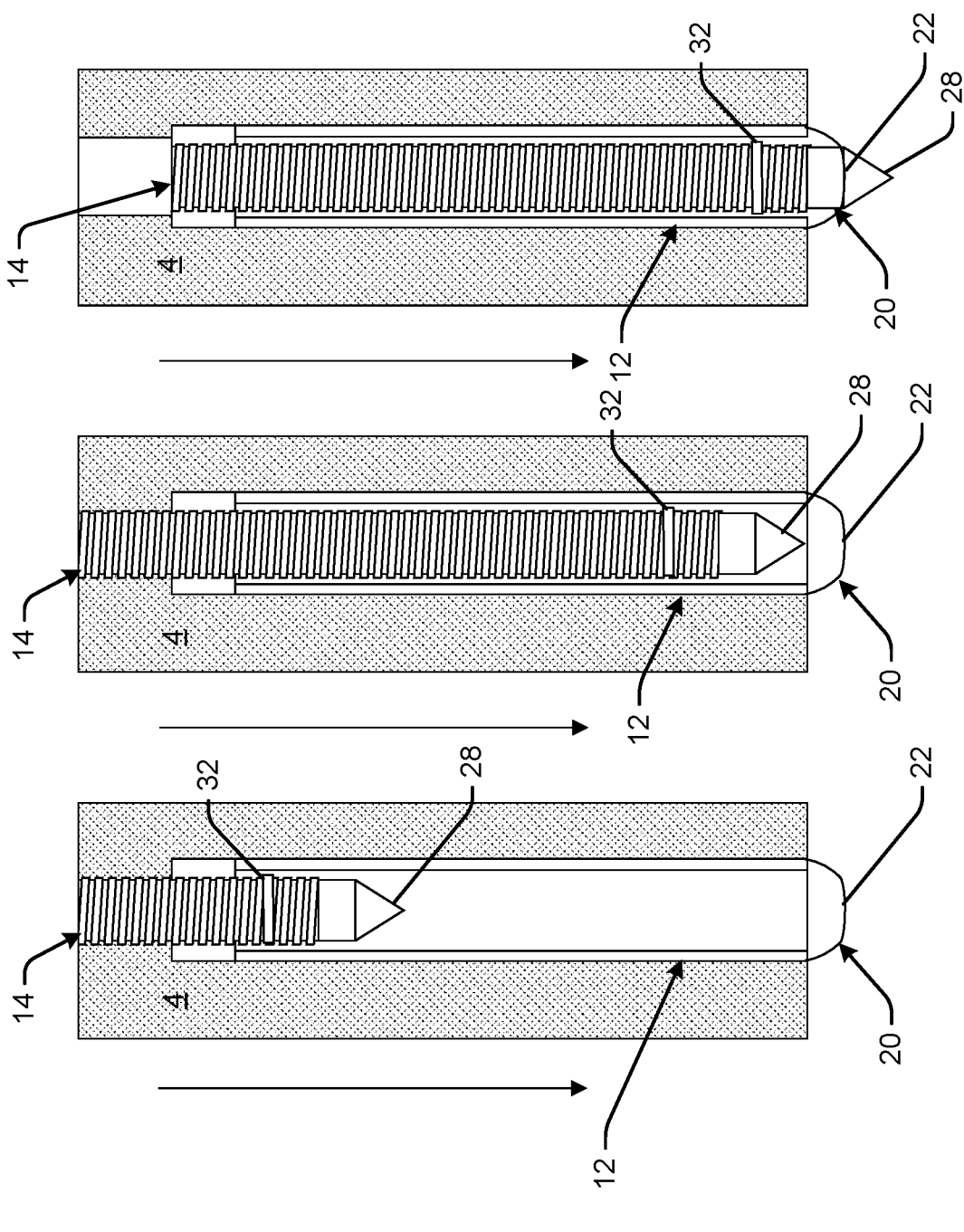
FIG. 6 illustrates an example sampling operation, wherein the sample drive rod is extended through the sample core barrel so that a pointed end of the sample drive rod extends beyond a soil cutting shoe of the sample core barrel.
Figure 7:
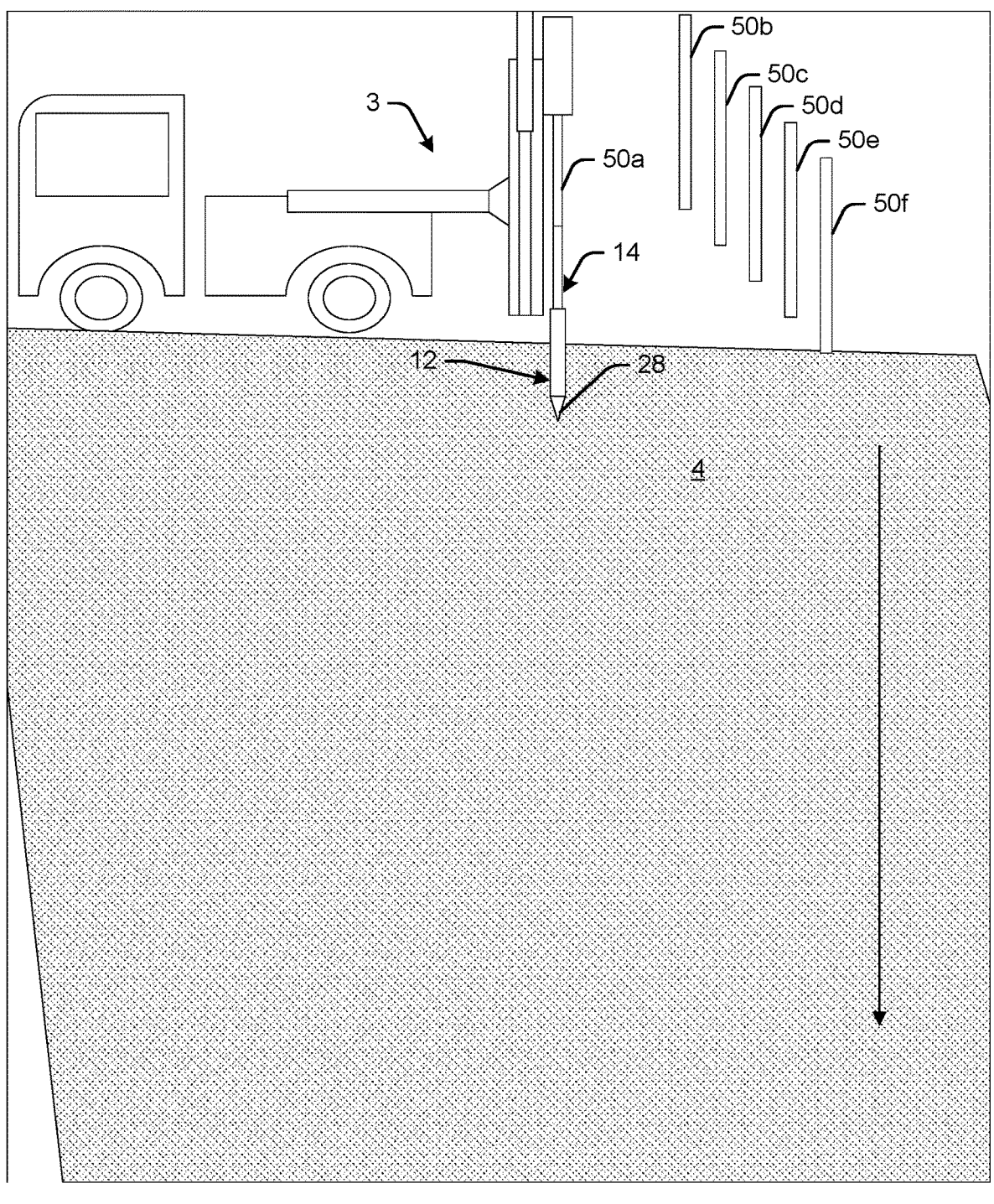
FIGS. 7-10 illustrate further example sampling operations, wherein the sample drive rod and the sample core barrel are drilled to a desired depth through one or more ground layers.
Figure 8:
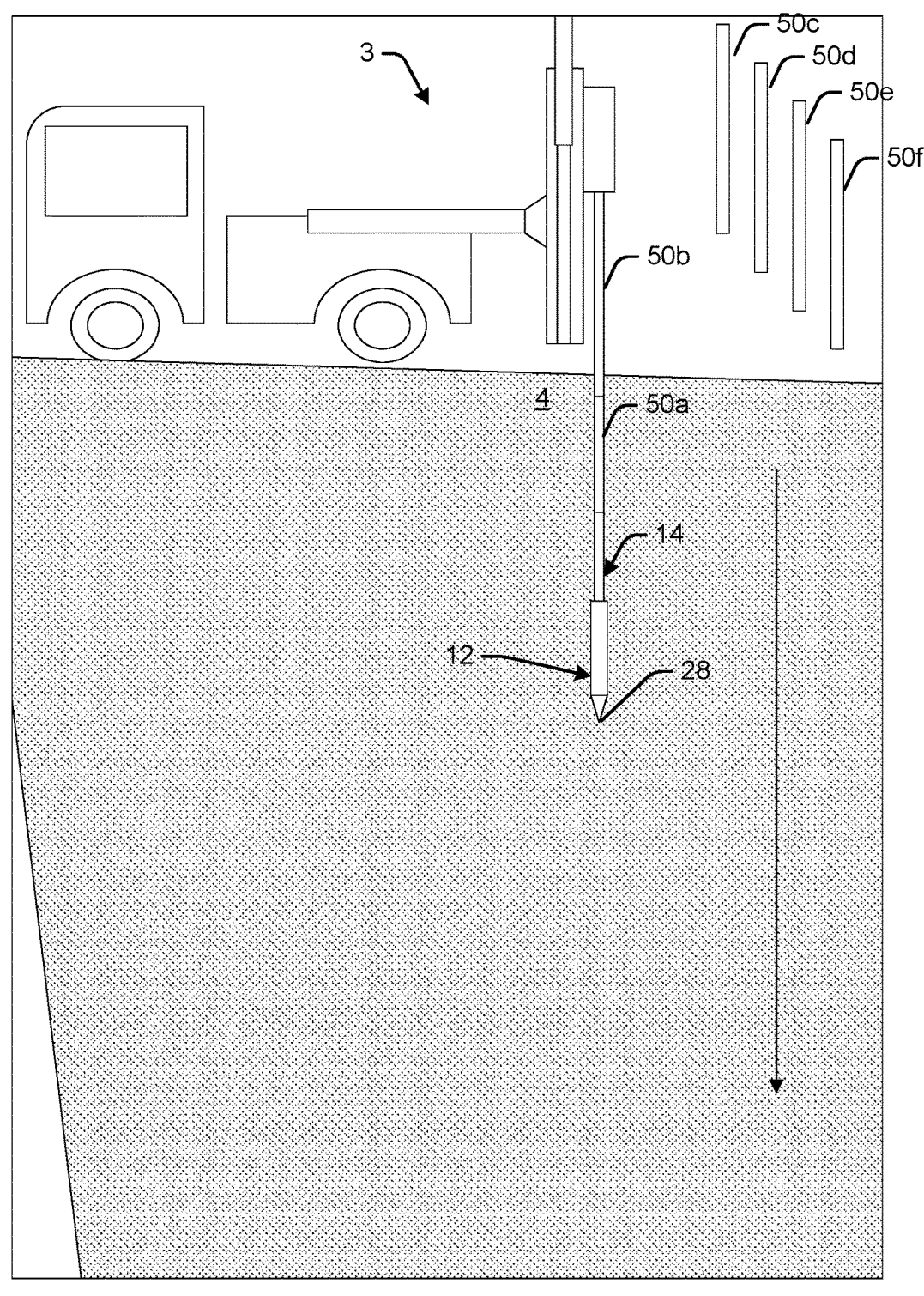
Figure 9:
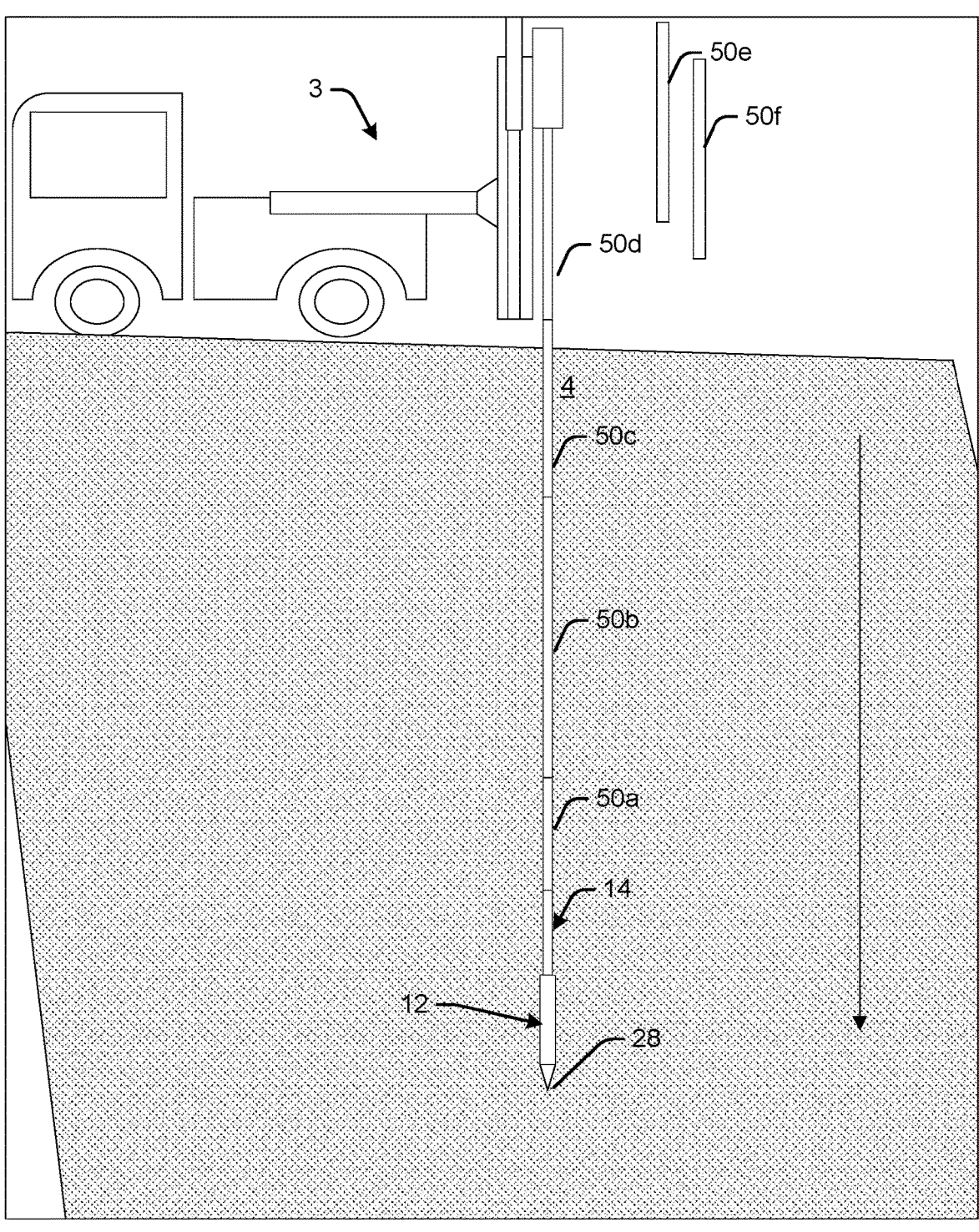
Figure 10:
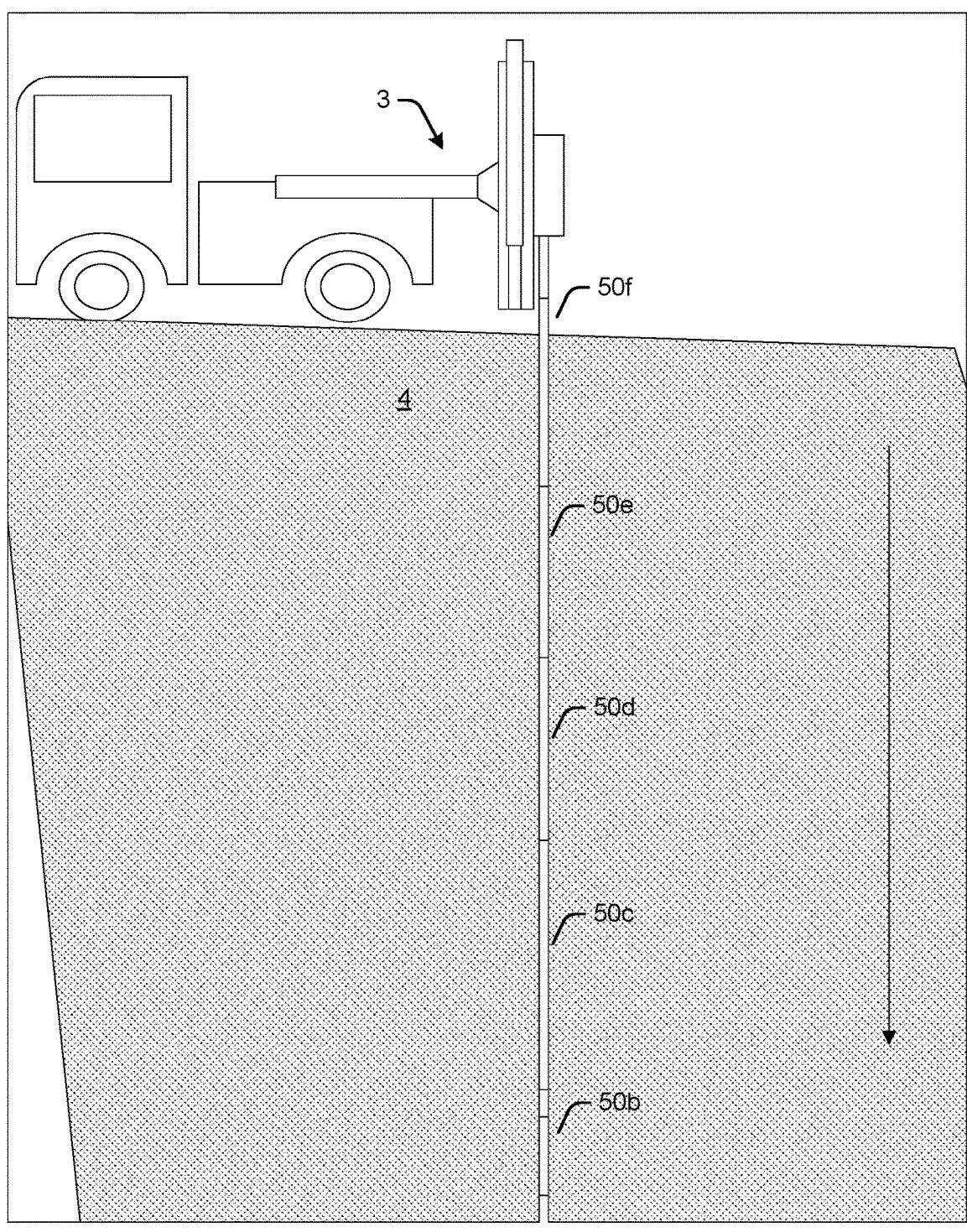

FIG. 6 illustrates an example sampling operation, wherein the sample drive rod 14 is extended through the sample core barrel 12 so that a pointed end 28 of the sample drive rod 14 extends beyond an opening of the soil cutting shoe 20 of the sample core barrel 14.

FIGS. 7-10 illustrate further example sampling operations, wherein the sample drive rod 14 and the sample core barrel 12 are drilled to a desired depth through one or more ground layers 4. Multiple drill rods 50a-f (of one or more length) may be needed to get to the determined depth for the sampling operation, while ensuring all percussion drill rod connections stay tight during the opening of the discrete soil sampler 10.

The example discrete soil sampler 10 may be drilled to the desired depth as follows. With a sample core barrel 12 locked on the sampler drive rod 14 to a specified torque, the example discrete soil sampler 10 is ready to be driven into the ground (see, e.g., FIG. 4). After the example discrete soil sampler 10 has been inserted into the ground, the user may add (e.g., screw on) a 1.5" outside diameter percussion drill rod 50a. This process may be repeated as necessary (e.g., with drill rods 50b-f until the sample core barrel 12 reaches the desired depth.

Figure 11:
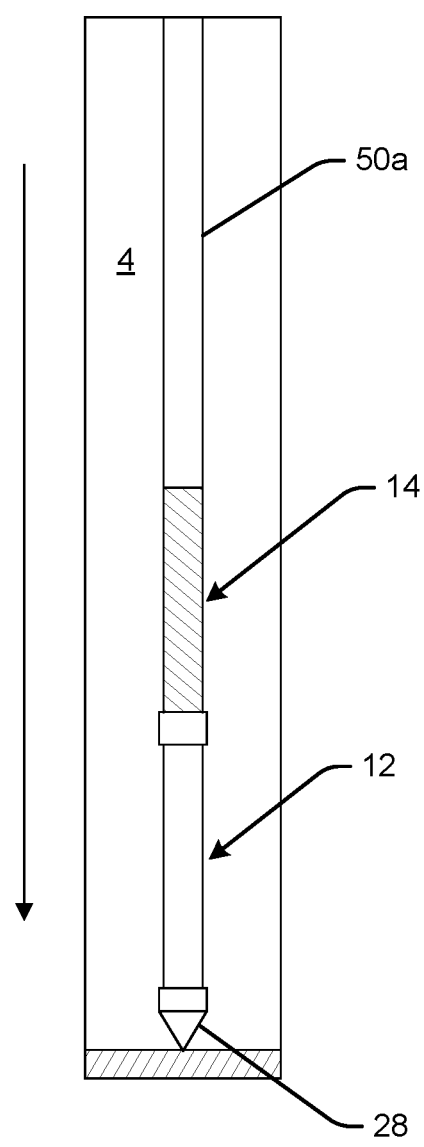
FIG. 11 is a close-up illustration showing the sample drive rod and sample core barrel reaching the desired depth during the example sampling operation.

FIG. 11 is a close-up illustration showing the sample drive rod 14 and sample core barrel 12 reaching the desired depth during the example sampling operation. The discrete soil sampler 10 sampling area can be opened (e.g., by withdrawing the sample drive rod 14 from the sample collection tube 26) and ready for soil sampling within 15 seconds upon arrival at its determined depth into the subsurface being sampled. The discrete soil sampler 10 requires no extruder rods for opening.

FIG. 12 is a close-up illustration showing the sample drive rod retracting from the sample collection tube 26 in the sample core barrel 12 during the example sampling operation. The entire string of drill rods 50a-f is turned to the right 50 rotations. The example discrete soil sampler 10 is now open to core up to 12" of soil sample. The sample core barrel 12 houses the clear polycarbonate round tube 26 that holds the soil samples once they have been collected.

The sample core barrel 12 is then driven one more foot to the desired depth into the soil 4. The discrete soil sampler 10 is now open to core up to 12" of soil sample. It is noted that the sample core barrel 12 (and/or corresponding sample collection tube 26) may be provided in various lengths and is not limited to the 12 inches in the illustration.

Figure 13:
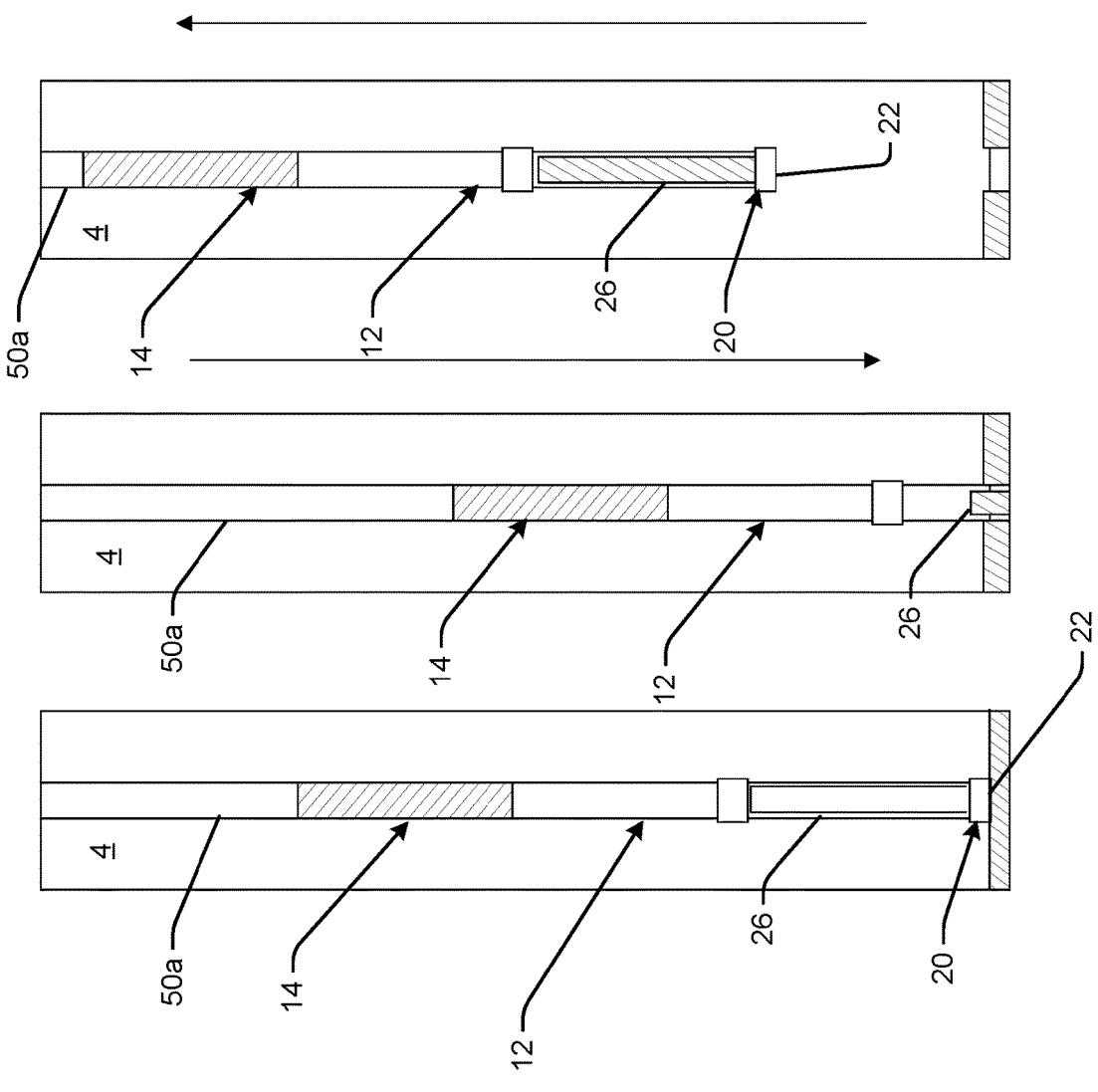
FIG. 13 is a close-up illustration showing the sample core barrel taking a soil sample during the example sampling operation.

The sample core barrel 12 enters the ground, driving the removable soil cutting shoe 20 for collecting soil samples. FIG. 13 is a close-up illustration showing the sample core barrel 12 taking a soil sample during the example sampling operation. During operation, the soil cutting shoe 20 enters the ground first when collecting soil samples. The sample core barrel 12 may then be withdrawn with the soil sample safely stored in the sample collection tube 26. The soil cutting shoe 20 may be tapered to minimize scraping soil off of the sides of the hole to preserve integrity of the soil sample.

Figure 14:
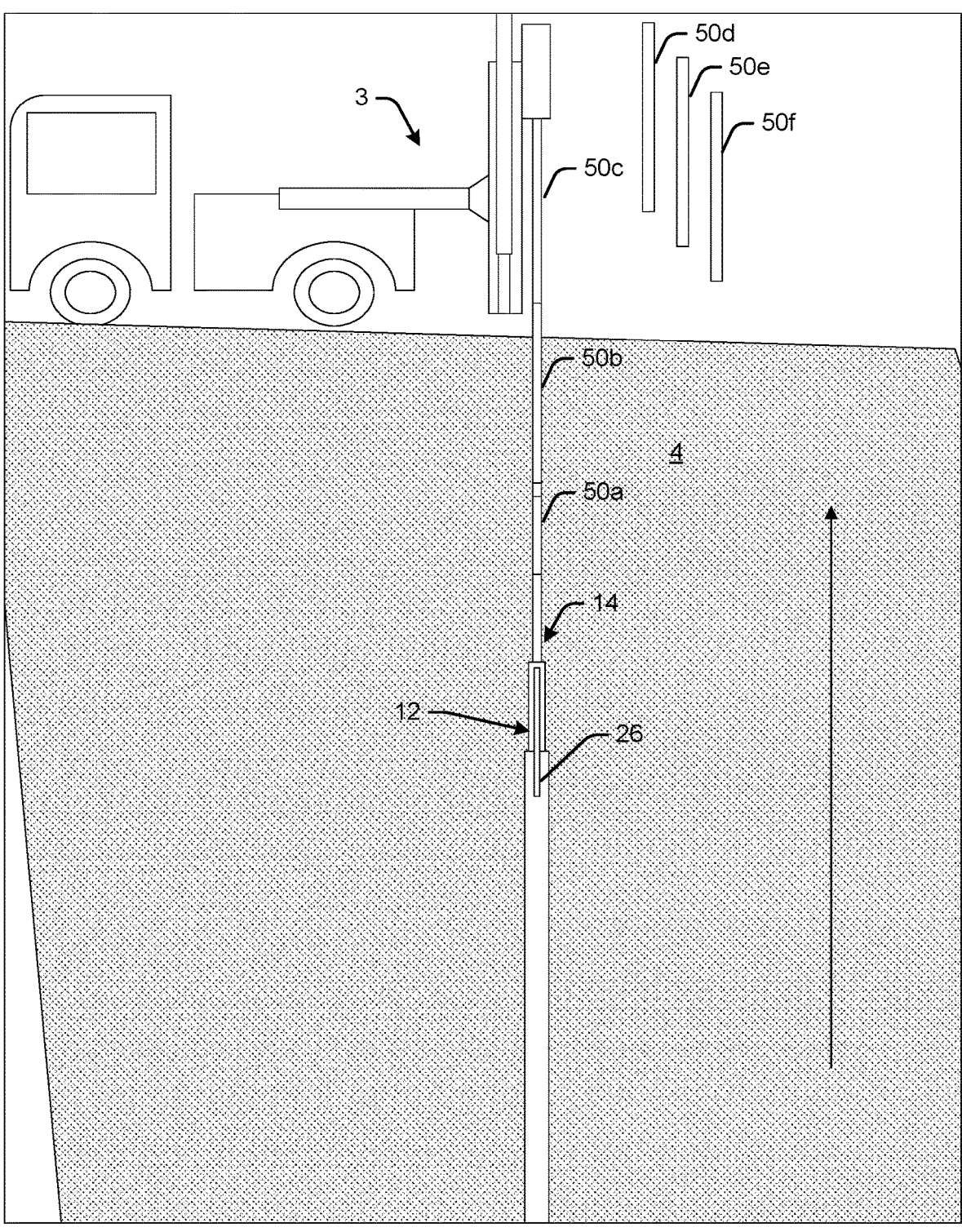
FIGS. 14-16 illustrate further example sampling operations, wherein the sample drive rod and the sample core barrel are withdrawn from the one or more ground layers.
Figure 15:
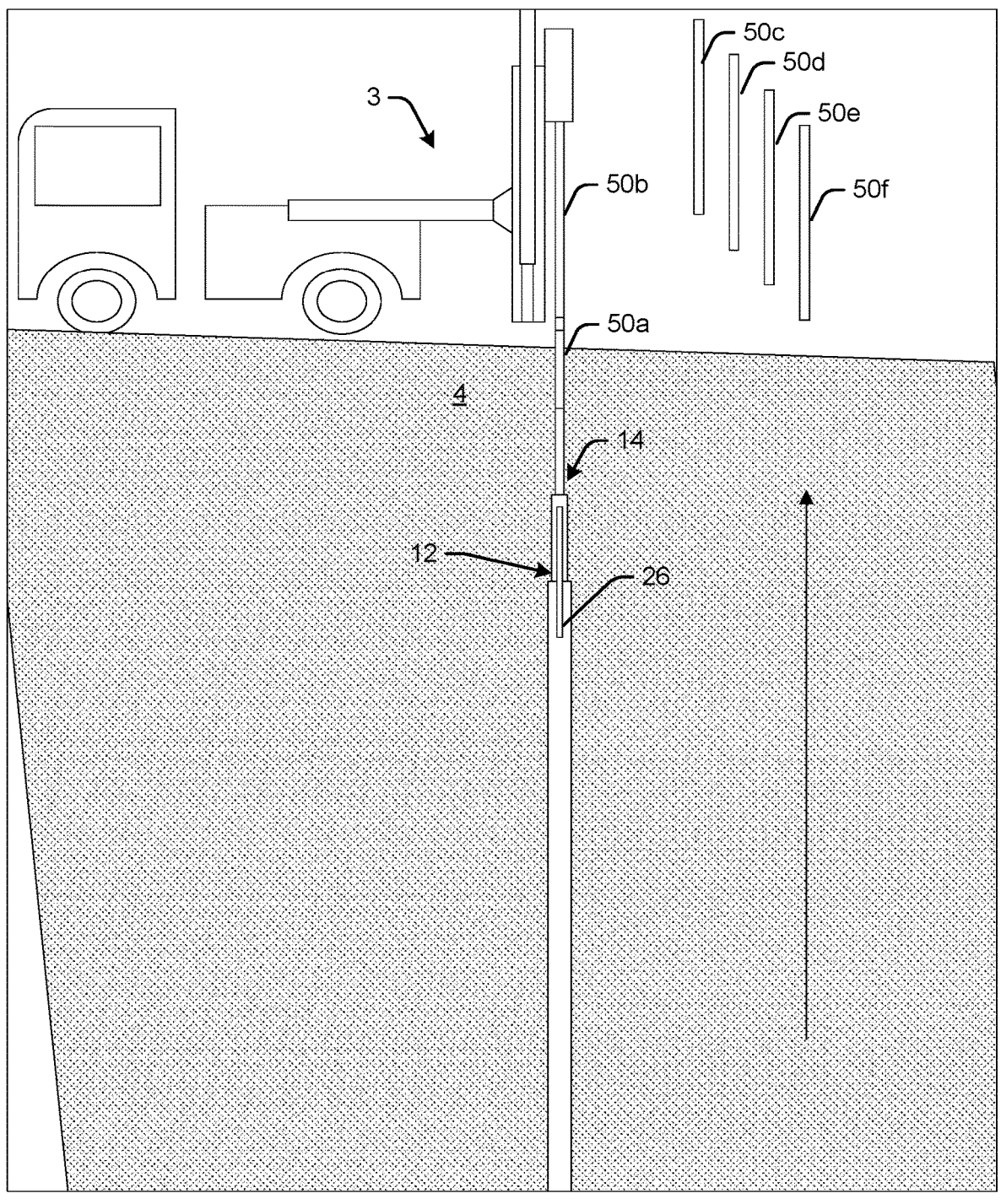
Figure 16:
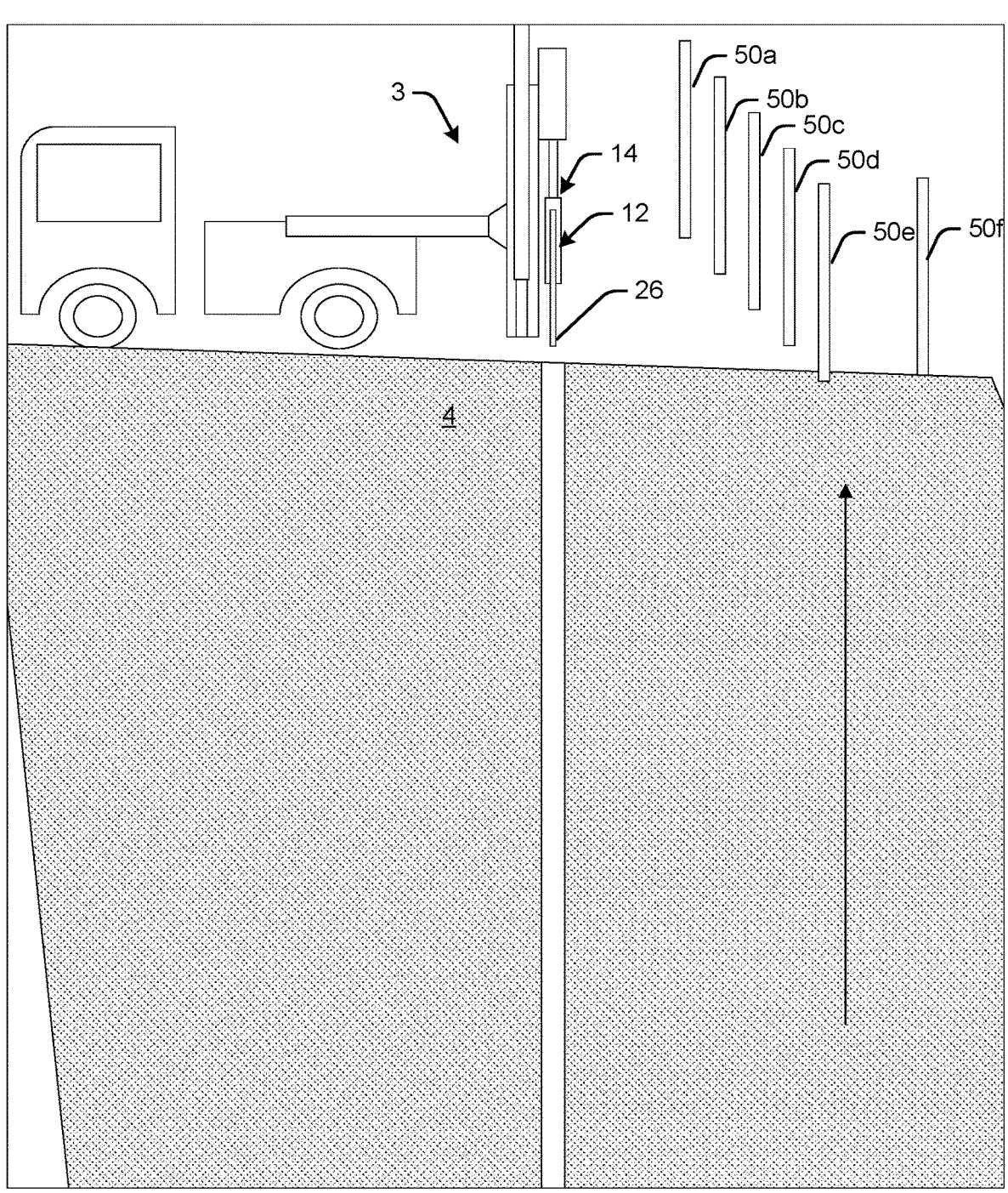

FIGS. 14-16 illustrate further example sampling operations, wherein the sample drive rod 14 and the sample core barrel 12 are withdrawn from the one or more ground layers. The sampling operation, the drill string 50a-f is retrieved from the core hole.

Figure 17:
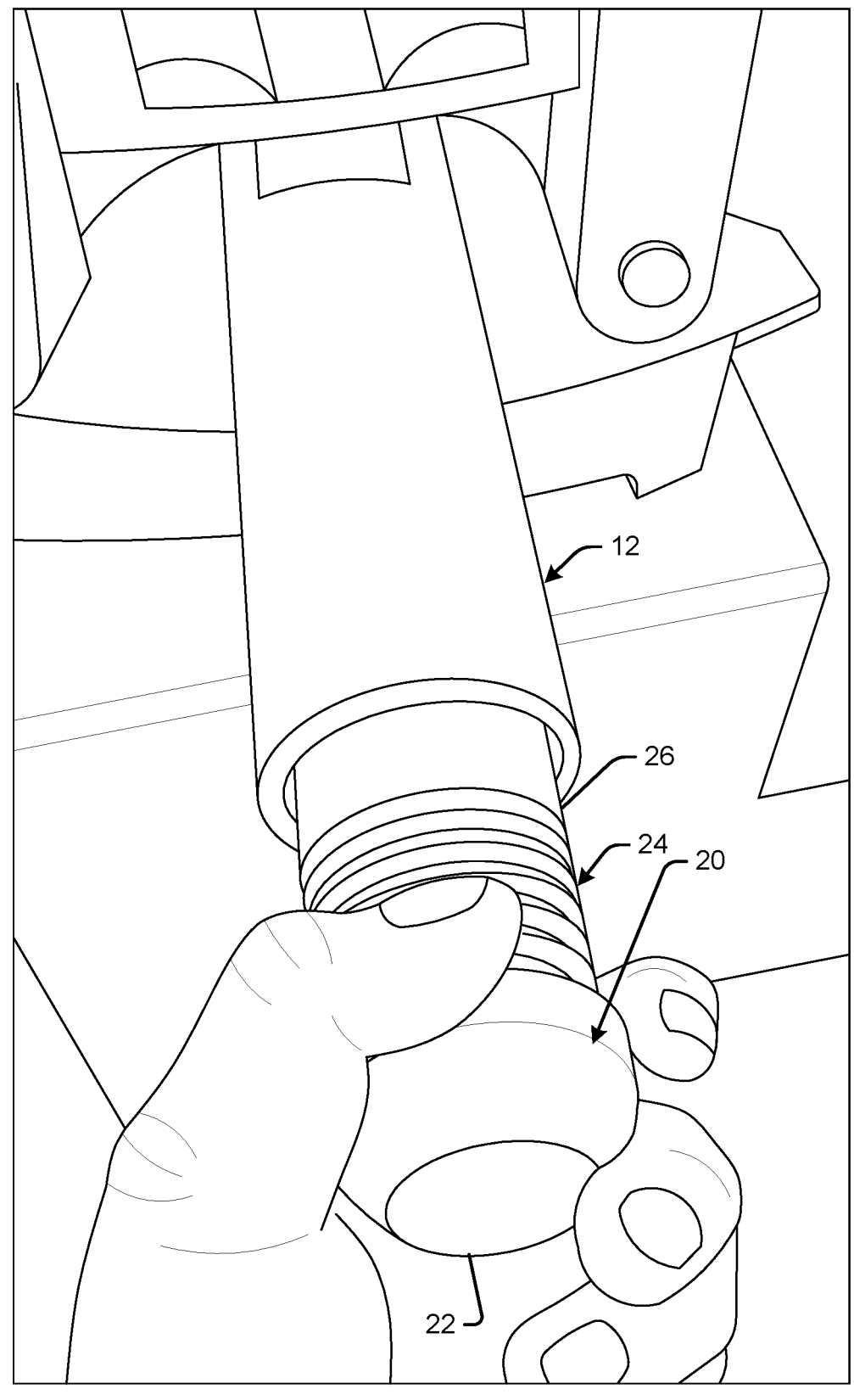
FIG. 17 is a close-up illustration showing the collection tube being removed from the sample core barrel after the sample core barrel has been withdrawn from the one or more ground layers during the example sampling operation.

FIG. 17 is a close-up illustration showing the collection tube 26 being removed from the sample core barrel 12 after the sample core barrel 12 has been withdrawn from the one or more ground layers during the example sampling operation. In an example, a sample core barrel 12 is provided with a removable cutting shoe 20 with attached clear polycarbonate round tube 26 so that soil samples will stay safe during the collection and retrieval process of soil samples. At the ground surface, the user can remove the cutting shoe 20 and slide out the clear polycarbonate round tube 26 to expose the soil sampled elements. FIG. 2 shows an example collection tube 26 of the example discrete soil sampler 10 after it has been removed from the sample core barrel 12.

It is noted that the examples shown and described are provided for purposes of illustration and are not intended to be limiting. Still other examples are also contemplated.

The invention claimed is:

1. A discrete soil sampler comprising:
   a single cylindrical core barrel having a driving end and a receiving end;
   a soil cutting shoe having a first end and second end;
   wherein the second end of the soil cutting shoe is attached to a collection tube;
   wherein the soil cutting shoe and the attached collecting tube, as a combined unit, are configured to coaxially and internally be received through the driving end of the single cylindrical core barrel, and the second end of the soil cutting shoe and the collection tube, as a combined unit, are also configured to be removably attached to the driving end of the single cylindrical core barrel;
   a sample drive rod with a pointed end which is movably received through the receiving end of the single cylindrical core barrel and movable through the collection tube and the soil cutting shoe and movable to an extended position and a retracted position;
   wherein at the extended position, the pointed end of the sample drive rod extends through an opening formed through the soil cutting shoe; and wherein at the retracted position, the sample drive rod is retracted from the collection tube.

2. A discrete soil sampler of claim 1, wherein the sample drive rod further comprises an attachment end configured to mate with a drill extension rod.

3. A discrete soil sampler of claim 1, wherein the driving end of the single cylindrical core barrel further comprises internal threading; and wherein the second end of the cutting shoe further comprises an external threading; wherein the internal threading of the driving end of the single cylindrical core barrel rotatably mates with the external threading of the second end of the cutting shoe.

4. A discrete soil sampler of claim 1, wherein the sample drive rod further comprises a dual percussion rod thread; and wherein the single cylindrical core barrel further comprises an internal thread configured to engage the dual percussion rod thread to move the sample drive rod between the extended position and the retracted position.

5. A discrete soil sampler of claim 4, wherein the first end of the soil cutting shoe further comprises an internal thread configured to engage the dual percussion rod thread.

6. A discrete soil sampler of claim 1, further comprising a stop on the sample drive rod configured to prevent the sample drive rod from being fully removed from the sample core barrel.

7. A discrete soil sampler of claim 6, wherein the stop on the sample drive rod comprises a recessed internal cut on a dual percussion rod thread of the sample drive rod.

8. A discrete soil sampler of claim 1, wherein the soil cutting shoe further comprises a cutting edge on the first end.

9. A discrete soil sampler of claim 8, wherein the cutting edge of the soil cutting shoe is tapered.

10. A discrete soil sampler of claim 8, wherein the sample drive rod further comprises a stop configured to prevent the pointed end from overextending out through the opening formed through the cutting edge of the soil cutting shoe.

11. A discrete soil sampler of claim 10, wherein the stop on the sample drive rod comprises a collar.

12. A method for obtaining a discrete soil sample comprising:

providing the discrete soil sampler of claim 1;

driving the discrete soil sampler with the sample drive rod at the extended position to a desired subsurface depth from which the soil sample is to be taken;

moving the sample drive rod to the retracted position;

driving the discrete soil sampler to a further subsurface depth and thereby obtaining the discrete soil sample in the collection tube.

13. A method for obtaining a discrete soil sample of claim 12, further comprising:

removing the discrete soil sampler from the subsurface;

detaching the soil cutting shoe and collection tube, together, from the single cylindrical core barrel;

detaching the collection tube from the soil cutting shoe.

14. A method for obtaining a discrete soil sample of claim 13 further comprising;

repeating the method of obtaining a discrete soil sample to obtain additional discrete soil samples at the same depth or different depths in the subsurface.

* * * * *